United States Patent
Evans et al.

[11] Patent Number: 4,535,285
[45] Date of Patent: Aug. 13, 1985

[54] APPARATUS FOR DETERMINING AN ELECTRICAL CHARACTERISTIC OF A FIBROUS DISPERSION

[75] Inventors: Brian E. Evans; Stephen R. Hemm, both of High Wycombe; Rupert A. V. Russell, London, all of England

[73] Assignee: The Wiggins Teape Group Limited, Hampshire, England

[21] Appl. No.: 439,406

[22] Filed: Nov. 5, 1982

[30] Foreign Application Priority Data

Nov. 9, 1981 [GB] United Kingdom ............... 8133786

[51] Int. Cl.³ ............................................. G01N 27/00
[52] U.S. Cl. .................................... 324/71.1; 324/425; 324/450; 162/49; 162/263; 204/1 T
[58] Field of Search ........................ 324/71.1, 71.4, 72, 324/439, 450, 453, 466, 425, 438; 73/61 R, 63; 204/409, 411, 412, 1 T; 162/49, 263

[56] References Cited

U.S. PATENT DOCUMENTS

| | | | |
|---|---|---|---|
| Re. 28,940 | 8/1976 | Komline, Sr. et al. | 324/92 |
| 2,252,222 | 8/1941 | Van Os | 324/71.4 |
| 3,461,030 | 8/1969 | Keyes | 162/198 |
| 3,723,712 | 3/1973 | Komline, Sr. et al. | 324/109 |
| 3,958,177 | 5/1976 | Reeves et al. | 324/71.1 |
| 4,253,329 | 3/1981 | Karnis | 73/63 |
| 4,254,377 | 3/1981 | Findl et al. | 324/453 |

FOREIGN PATENT DOCUMENTS 2326409 12/1974 Fed. Rep. of Germany .......... 80/94

OTHER PUBLICATIONS

Sack, W., Kontinuierliche Stromungspotentialmessung an einer PM, Das Papier 30, No. IDA, pp. V42–V46, 1976.

Primary Examiner—Michael J. Tokar
Assistant Examiner—Kevin D. O'Shea
Attorney, Agent, or Firm—Burns, Doane, Swecker & Mathis

[57] ABSTRACT

In the formation of a paper web from stock fed to a Foudrinier wire, the Zeta Potential is an important parameter. A measure of Zeta potential is made by measuring the streaming potential developed in a vertically-arranged cell having a horizontal mesh therein on the underside of which a pad of fibres and fines is formed by pumping stock into the lower part of the cell. Electrodes located in the cell above and below the pad are used to obtain a measure of streaming potential at a given pressure differential across the pad. A pressure transducer is mounted in the lower part of the cell. Corrections are made for temperature and conductivity by sensors in the stock feed path to the cell. A microprocessor control and measuring circuit is disclosed which sequences valves for controlling the flow of stock and flushing fluid to the cell and which measures the relevant parameters.

23 Claims, 10 Drawing Figures

APPARATUS FOR DETERMINING AN ELECTRICAL CHARACTERISTIC OF A FIBROUS DISPERSION

FIELD OF THE INVENTION

This invention relates to an apparatus and method for determining an electrical characteristic of a fibrous dispersion. A particular application of the invention is to the measurement of an electrical characteristic known as streaming potential in the feed stock or furnish supplied to a paper making machine. The invention will be described in relation to apparatus for monitoring streaming potential and to a system for controlling such potential. The invention also relates to a measuring cell for use in such measurements.

BACKGROUND TO THE INVENTION

In recent times much attention has been given to the effects of Zeta poential on the retention and formation of paper on the wire of a paper making machine. Zeta potential is an electrokinetic phenomenon associated with the charge developed on the particles that are suspended in the water of the feed stock or furnish and is affected by ion-producing chemicals commonly added to the paper for various purposes.

Zeta potential is usually measured in an indirect way by measuring a parameter dependent on it. One parameter used for the purpose is known as streaming potential, a potential difference which is established by the flow of liquid past stationary charged particles. A general discussion of Zeta potential and its effect is to be found in the paper "Electrokinetics in Papermaking—a Position Paper" by R. A. Stratton and J. W. Swanson in TAPPI, 64 No. 1, Page 79 (1981). Further discussion of Zeta potential together with a description of a system for measuring streaming potential is disclosed in the paper "Continuous Measurement of the Streaming Potential on a Paper Machine" by W. Sack of F. Schoeller, Jnr., in Das Papier 30, No. 10A, V42–V46 (1976).

What is clear from these papers is that while Zeta potential has an undoubted influence on paper formation, e.g. retention on the wire, flocculation and drainage, its effects cannot be quantified precisely. The optimum Zeta potential in a particular case depends on the paper to be made and hence the nature of the feedstock, including additives, and the characteristics of the paper-making machine in question. The work done so far, however, suggests that in most cases it is desirable to prevent excessive Zeta potential developing and that commonly it is required to maintain the Zeta potential at or near zero value for optimum results as regards the formation of paper on the wire.

Whatever the significance of Zeta potential and the mechanisms by which it influences paper formation in a particular case, there is a general need to be able to exercise control of Zeta potential in a paper-making process and consequently to be able to make a measure of it or of one of its dependent parameters such as streaming potential. The present invention is concerned with apparatus that is capable of making a measurement of streaming potential and with a control system including such measuring apparatus that is capable of maintaining the measured streaming potential at a set level which may be, but is not necessarily, zero.

The Sack paper above-mentioned describes an apparatus for measuring streaming potential in which a sample stream of white water—that is water drained from the wire—is passed through a horizontal cell in which the water is filtered by a vertical wire mesh on which a plug of the fibres and other particles in the water is built up. The streaming potential is developed across the plug and is measured by electrodes disposed in the cell on opposite sides of the plug (also referred to herein as a pad). The making of a further measurement requires rinsing of the cell to remove the plug and the establishment of a fresh plug.

While the Sack paper refers to the sample being white water or stock from the breastbox it appears from the paper that the measurements were all made on white water. It is generally desirable to provide apparatus that can be used reliably with the feed stock from the breastbox. The white water will contain a higher proportion of small fibres and fines since the larger fibres will be trapped on the wire.

There are factors which may, in our opinion, contribute to the Sack apparatus being unsatisfactory for practical use. In the horizontal cell shown there will be a tendency to sedimentation as the plug builds up leading to non-uniform plug, that is a wedge-shaped plug thicker at the lower part of the cell. This tendency would be even greater in measurements made on the feed stock than on the white water. In addition proper rinsing or flushing of the cell may be difficult to achieve consistently in the horizontal cell. The plug or pad is compacted to a degree that causes it to be released as a substantially unitary body. This body must be removed as completely as possible together with any remaining particles on the filter structure. Furthermore, the streaming potential measurement as made by Sack and which is dependent on the pressure difference across the plug, is made during build-up of the plug. The potential is taken as the difference between the potentials measured as a low pressure limit is exceeded as the plug starts to build up and as a high pressure limit is reached when the plug is far more fully formed. Consequently, the measurement is not made with the same plug. It is not necessary here to enter into a full discussion of streaming potential and the factors that affect it. Reference may be made to "Colloid Science"—Vols. I and II; Editor: Kruyt; published by Elsevier.

There will be described hereinafter apparatus in accord with the present invention which is intended to at least mitigate the disadvantages set forth above so as to lead to measurements of sufficient reliability to be used in the control of a paper-making machine.

SUMMARY OF THE INVENTION

According to one aspect of the present invention there is provided a measuring apparatus for use in the measurement of an electrical characteristic of a fibrous dispersion. The apparatus comprises a measuring cell having a housing defining a hollow interior, upper and lower ports in said housing to allow fluid to be passed therethrough in a generally vertical direction, and an essentially horizontally disposed filter mesh in the housing dividing said interior hollow into upper and lower compartments. A respective electrode is located in each of the compartments for measuring the streaming potential generated in the cell. The apparatus also comprises respective first and second fluid conduit arrangements connected to the upper and lower cell ports respectively. The first conduit arrangement includes respective connections for a source of flushing fluid and drain, and valve means for controlling the flow of fluid through these connections. The second conduit arrangement includes respective connections for a source of particle-bearing stock and drain, and valve means for controlling the flow of fluid through these last-mentioned connections.

For pressure measurement in using the cell for monitoring streaming potential, the measuring cell preferably comprises a pressure transducer responsive to the pressure in the lower compartment. The apparatus may also be adapted to measure temperature and conductivity which are factors influencing streaming potential. This may be measured by devices located in the conduit leading to the lower port.

The measuring cell may comprise an apertured, inverted frusto-conical member disposed in the upper cell compartment to assist in the distribution of flushing fluid entering the upper port over the filter mesh to remove a pad formed on the mesh. The lower edge of the member is preferably spaced from the adjacent interior surface of the housing to allow access of the flushing fluid to the outer periphery of the pad. A preferred housing defines the interior hollow to have an intermediate section in which the filter mesh is supported, an upper end section of frusto-conical internal form narrowing upwardly to the upper port and a lower end section of frusto-conical internal form narrowing downwardly to the lower port.

For regular use of apparatus of the invention it is generally desirable to make it as easy as possible to replace the filter mesh which will need changing from time to time. In another aspect of the invention there is provided a measuring cell comprising an upper housing section defining an interior frusto-conical surface narrowing upwardly to an upper port in the upper housing section. The cell further comprises a lower housing section defining an interior frusto-conical surface narrowing downwardly to a lower port in the lower housing section. An intermediate section is located between the lower and upper housing sections and comprises a carrier member having an aperture at which the filter mesh is received, the carrier member being mounted for sliding movement between a first, operative, positive in which the filter mesh is disposed between the upper and lower housing sections and a second, filter-changing, position in which the filter mesh is to one side of the upper and lower housing sections. Respective sealing means are provided between the upper and lower housing sections and the carrier member to provide a sealed enclosure for the filter mesh in the operative position.

Preferably releasable means act between the upper and lower housing sections being operative in a locked or tightened condition to ensure the sealing action of the sealing means in the operative position of the carrier and in the released condition allowing movement of the carrier to the filter-changing position. The carrier member is conveniently planar and slidable between facing surfaces of the upper and lower housing sections. The filter aperture is located at one end portion of the carrier and the sealing means are conveniently respective annular rings carried in recesses or rebates of the facing housing surfaces to encircle the aperture in the operaive position and sealingly engage the surrounding carrier surfaces.

In a preferred construction the upper and lower housing sections have flanges extending in and to one side of the carrier with respect to its direction of movement and the releasable means act between the flanges. The releasable means may simply be nut and bolt fastenings with spacers located between the flanges. Preferably a manually-actuable, cam arrangement is provided for easy movement between the locked and released conditions. Preferably guide means, such a rollers, are located between the flanges to guide the sliding movement of the carrier. These rollers may, for example, be supported by the spacers.

In a preferred apparatus to be described the valve means of the first conduit arrangement comprises first and second valves connected between the upper port and respectively the flushing fluid connection and drain connection. The second valve means comprises third and fourth valves connected between the lower port and respectively the feed stock connection and drain connection. Furthermore the first conduit arrangement comprises a pump connected between the feed stock connection and the third valve for pumping feed stock to the lower port, and a flow diversion path comprising restrictor means and a fifth valve connected between the pump and third valve for establishing a predetermined pressure determined by the restrictor means.

The measuring apparatus further comprises control means coupled to the first to fifth valves to control the actuation thereof in a predetermined sequence including the steps in which (a) the second and third valves are open and the first, fourth and fifth valves are closed to allow feed stock to be pumped upwardly through said measuring cell to drain to thereby form a pad on the filter mesh;

(b) the second, third and fifth valves are open and the first and fourth valves are closed to establish a pressure determined by said restrictor means in said lower cell compartment to act upon the pad on the filter mesh;

(c) the first and fourth valves are open and the second and third valves are closed to cause flushing fluid to flow downwardly to drain thereby removing the pad and flushing the material thereof to drain; and (d) between steps (a) and (b) and/or between steps (b) and (c), the second, third and fourth valves are open and the first valve is closed to establish a low pressure reference condition in the lower cell compartment.

A measuring apparatus controlled as just stated and including the earlier-mentioned pressure transducer, may further comprise for the measurement of streaming potential, signal processing means connected to the electrodes and the pressure transducer, the signal processing means being operable to take measurements of streaming potential and pressure during the above step (b) and during the above step (d) at the or each occurrence thereof, and to calculate a measure of the ratio of streaming potential to pressure during step (b) referred to the valves obtained in step (d). Preferably the signal processing means is operable to respectively sample the streaming potential and pressure values during each step and to perform the calculation using averages obtained from the repetitive sampling in each step.

In another aspect of the invention there is provided a method of obtaining a measure of streaming potential using a measuring cell having a housing defining a hollow interior, upper and lower ports in said housing to allow fluid to be passed therethrough in a generally vertical direction, and an essentially horizontally disposed filter mesh in said housing dividing said hollow interior into upper and lower compartments, a respective electrode in each compartment for measuring streaming potential generated in the cell, and a pressure transducer responsive to pressure in said lower compartment, the method comprising the steps of:

(a) introducing feed stock containing particulate material to said lower port to flow upwardly through the cell and develop a pad of such material on said filter mesh;

(b) applying a pressure pulse to said pad and measuring the streaming potential across said electrodes and the pressure in said lower compartment;

(c) reducing the pressure across the pad to substantially zero prior and/or subsequent to step (b), and measuring the streaming potential and pressure in the lower compartment at the or each occurrence of the substantially zero pressure; and determining the ratio of streaming potential to pressure in step (b) where the values in step (b) are taken relative to the values obtained in step (c).

Preferably in performing the above method measurements of streaming potential and pressure in the respective steps are performed by taking a series of measurements and averaging the measurements taken in each series.

In addition a temperature measurement may be taken and the ratio of streaming potential to pressure corrected by multiplying same by a temperature-dependent factor. Also a measurement of conductivity may be taken and the ratio of streaming potential to pressure or of temperature-corrected streaming potential to pressure, as the case may be, multiplied by a conductivity-dependent factor normalised to a predetermined conductivity value.

BRIEF DESCRIPTION OF THE DRAWINGS

Embodiments of the invention for the measurement of streaming potential will now be described with reference to the accompanying drawings in which.

DESCRIPTION OF THE EMBODIMENTS

Figure 1:
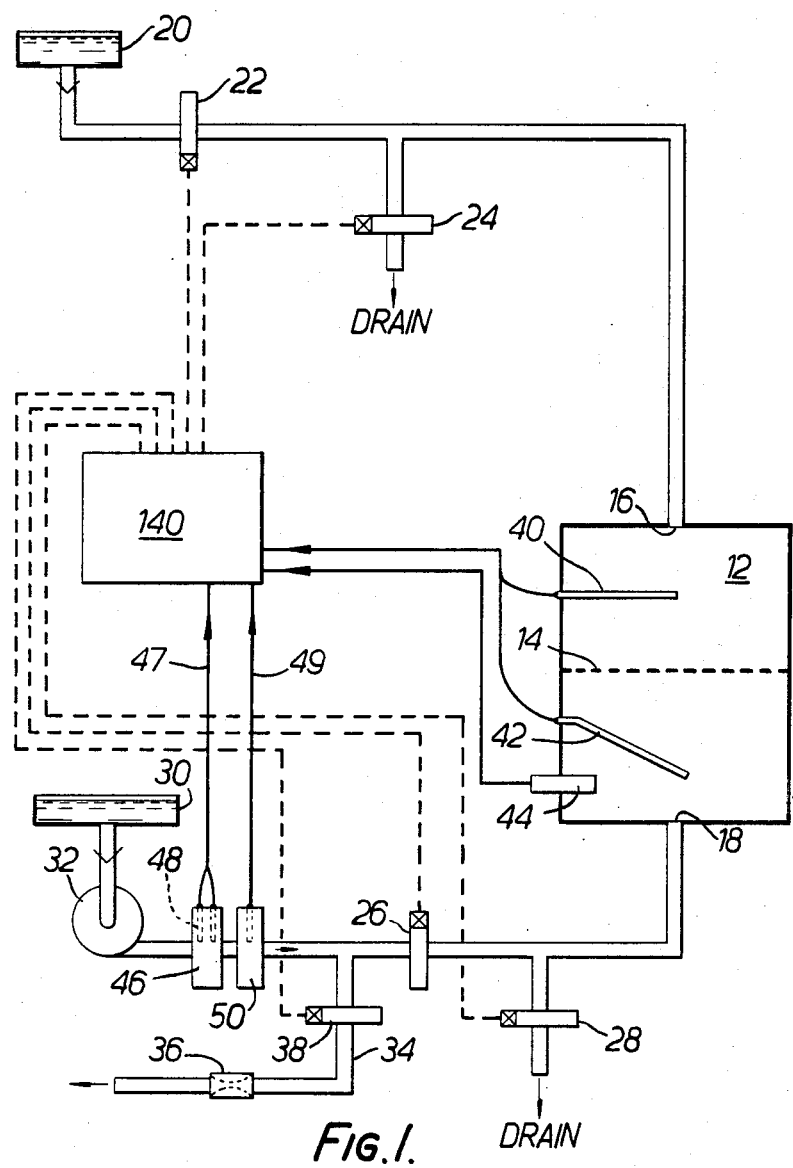
FIG. 1 shows the hydraulic circuit of an apparatus embodying the present invention.

Referring to FIG. 1, there is shown an apparatus 10 having a measuring cell 12 whose construction is described in greater detail below. The cell is vertically oriented as regards fluid flow therethrough and has a horizontal wire mesh 14 acting as a filter under which the fibrous plug or pad is formed.

The top and bottom of the cell 12 is provided with ports 16 and 18 for respective conduits that are each inlet and outlet conduits at different stages in the cycle of operation. Upper port 16 is selectively connectable to a pressure source of clean water 20, e.g. mains water, via a valve 22 or to drain (ambient) via valve 24. Lower port 18 is selectively connectable to a source of feed stock via valve 26 or to drain via valve 28. The stock, which will be assumed to be tapped from the breastbox 30 of a paper making machine, is pumped to the cell by pump 32 through a valve 31 which is normally in the position shown. The valve 31 may be changed over to connect the pump inlet to the fresh water supply 20. On the pump side of valve 26 a diversion path 34 is provided from the pump, the path including a restrictor 36 and a further valve 38 in series with it. Stock diverted through the restrictor is discharged to any convenient point.

The valves 22, 24, 26, 28 and 38 are simple on-off control valves and are conveniently solenoid-actuated valves controlled by an electrical circuit which is indicated at 140 in FIG. 1 and which is to be more fully described with reference to FIG. 3. The control connections to the valve solenoids are indicated by broken lines. The valve 31 is manually operable to enables fresh water to be pumped through the cell 12 with valve 24 open to ensure expulsion of air when the instrument is first used or after a change of the filter mesh 14. For the following description valve 31 will be assumed to be in the position connecting the pump to the breastbox 30.

To flush or rinse the cell 12, valves 22 and 28 are opened and valves 24 and 26 closed. Clean water thus flows downwardly to drain through the measuring cell and release a pad previously formed on the lower side of filter mesh 14, which release and clearance from the vertically-oriented cell is aided by gravity. To form a pad, the valves 22, 28 and 38 are closed and valves 24 and 26 are opened so that stock may be pumped into the lower part of the cell 12 to form the pad on the lower side of the filter mesh 14, the filtered stock being discharged to drain through valve 24. The closure of valve 38 ensures that the pad is built at a higher pressure than that at which measurement is made. The higher pressure formation ensures the pad is stable mechanically over the measurement pulse to be described. The foregoing is a simplified explanation of operation of the cell. The measurement cycle, including the purpose of the diversion path 34, is explained in more detail below.

To measure the streaming potential developed across the pad the upper and lower chambers of the measuring cell 12 (above and below mesh 14) have respective electrodes 40, 42 mounted therein and the lower chamber also has a pressure transducer 44 for sensing the pressure acting on the filter mesh 14. Pressure is measured relative to ambient. The transducer is of a type that produces an electrical output signal. The signals from electrodes 40, 42 and transducer 44 are supplied to the circuit 140 as indicated by the full line connections. The circuit 140 serves both for control and signal processing and calculation functions.

In addition the conduit leading to the cell port 18 is fitted with two further sensors located between pump 32 and the diversion path junction. One is a liquid conductivity sensing element 46 having a pair of measuring electrodes 48. The other is a temperature sensing element 50. Both these sensors produce electrical signals that are taken to circuit 140 over leads 47 and 49 respectively.

Figure 2:
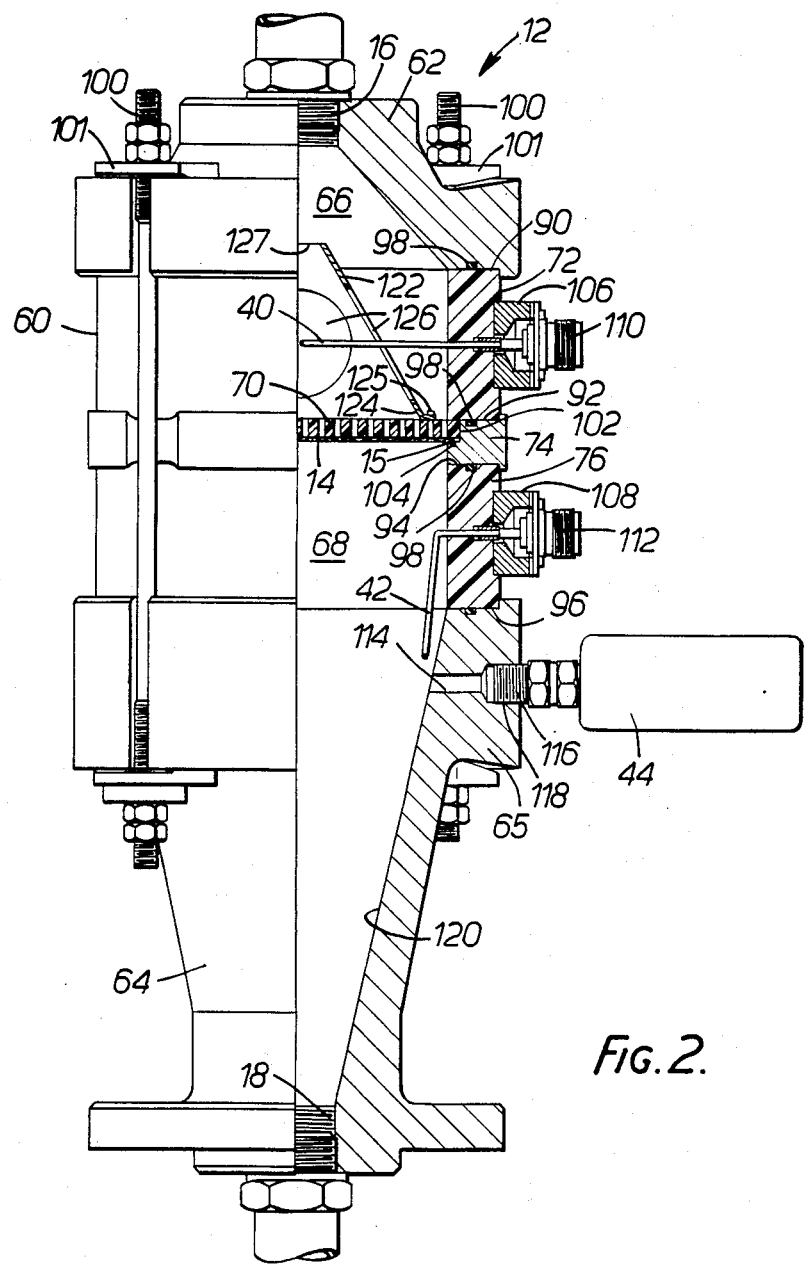
FIG. 2 shows in enlarged part-sectional view the measuring cell of FIG. 1 in which the fibre pad is formed.

The structure of a preferred form of measuring cell is shown in FIG. 2 in a half axial section. The cell 12 comprises a housing 60 of a generally cylindrical form having its longitudinal axis vertical. The housing of say 80 mm, internal diameter, is conveniently of a clear plastics material, e.g. perspex, to enable the interior of the cell to be readily inspected. The housing has top and bottom end closure members 62 and 64 having substantially frusto-conical interior surfaces leading to the respective ports 16 and 18 aligned on the axis with appropriate fittings for connection to the conduits shown in FIG. 1. The housing is also of a thick-walled construction, say 20 mm., not only to give overall strength and rigidity to the cell but to provide an adequate support for sensing elements mounted in the walls. The cell 12 is divided into upper and lower chambers 66 and 68 respectively by a perforated plastics disc 70 on the lower surface of which is secured the wire mesh 14. This disc is thick enough to provide a rigid support for the wire mesh 14 whose mesh size is in the range of say 20–200 microns. The disc perforations are numerous and of sufficient size to ensure a free flow of liquid through the disc so that the filtering action is performed by mesh 14. A plastics material rather than metal is preferred for the disc 70 to prevent corrosive electrolytic action with the filter mesh 14. The latter may be of stainless steel. The filter mesh is provided around it peripheral margin 15 with a coating of a silicone rubber compound on the both surfaces of the mesh. This aids in sealing the periphery of the filter assembly as will be described below.

The structure of the cell housing 60 allows ready disassembly for cleaning or replacement of the elements within the housing. The structure is also designed to promote even pad building on mesh 14 and to allow the easiest possible removal of the pad from the cell on flushing. As already mentioned, the pad is released as an essentially unitary body.

More particularly the housing comprises in sequence from top to bottom, the end member 62 in the form of an inverted, shallow funnel-shape, an upper cylindrical section 72, an annular ring 74, a lower cylindrical section 76 and the lower end member 64 of a longer more acute funnel-shape. The upper cylindrical section 72 is located axially and radially by rebates 90 and 92 respectively formed in the lower surface of member 62 and upper surface of ring 74. Similarly the lower cylindrical section 76 is located axially and radially by respective rebates 94 and 96 in the lower surface of ring 74 and upper surface of lower end member 64. O-ring seals 98 are located to act between the respective contacting surfaces of these housing parts. The housing parts have a thickness sufficient to take axially-extending bolts or studs 100 under the pressure exerted by which the housing parts are sealingly united. Four such bolts may be provided around the periphery of the housing. Two are shown and large washers 101 are provided to spread the clamping load around the housing.

The shaping of the funnel provided by lower member 64 is of importance in that it affects the build-up of a pad when stock is admitted through lower port 18. The stock should be distributed evenly and smoothly over the filter mesh and to this end flow dynamics require that the apex half-angle of the conical surface 120 within member 64 should not exceed about 7°. The end member 64 has a smooth frusto-conical interior surface 120 so as to lead smoothly from the lower end of cylindrical section 76 to the lower port 18 to aid in the flushing out of a fibre pad body which folds as it descends toward the port 18.

The ring 74 is provided with an interior rebate 102 which is sized to trap the peripheral margin of support disc 70 and that, 15, of the wire mesh 14 in a recess 103 formed with upper cylindrical section 72. An O-ring seal 104 contacts the silicone rubber compound on the margin of the mesh to prevent leakage past the periphery of the disc and mesh assembly.

Received in the relatively thick side walls of the upper and lower cylindrical sections 72 and 76 are respective bushes 106 and 108 from which the electrodes 40 and 42 respectively project into the interior of the housing in the respective compartments 66 and 68 above and below the filter assembly. The electrodes are of like material—stainless steel is suitable. It will be noted that the lower electrode is bent sharply downwardly—approaching 90°—to cause least impediment to the removal of a pad in the flushing phase. The bushes 106 and 108 have external connectors 110 and 112 respectively of any appropriate type for connecting their respective electrodes to the external circuitry.

The lower end member 64 has an enlarged upper end portion 65 abutting cylindrical section 76 and which has a radial hole 114 leading from the interior of the lower compartment 68, to a threaded bore 118 in which is received (i.e. screwed) an input fitting 116 of a pressure transducer 44 which converts sensed pressure to a corresponding electrical signal.

In the upper housing compartment 66 is located a flow distribution member 122 in the form of an inverted frusto-cone having an annular flange 124 that is secured to the disc 70 by a number of screws as shown at 125. It is noted that the flange 124 sits on the top surface of disc 70 spaced from the adjacent wall of compartment 66. The cone contains a number of sizable apertures 126 in its wall in addition to the central opening 127 at the top. The provision of the apertured cone is intended to provide a more even distribution of flushing water over the filter assembly to release the pad formed on the assembly. The flushing water is distributed axially through opening 127 to the central part of the pad and to outer portions through apertures 126. In addition the spaced relationship with the compartment wall allows the flushing water to act directly at the periphery of the pad.

Figure 4:
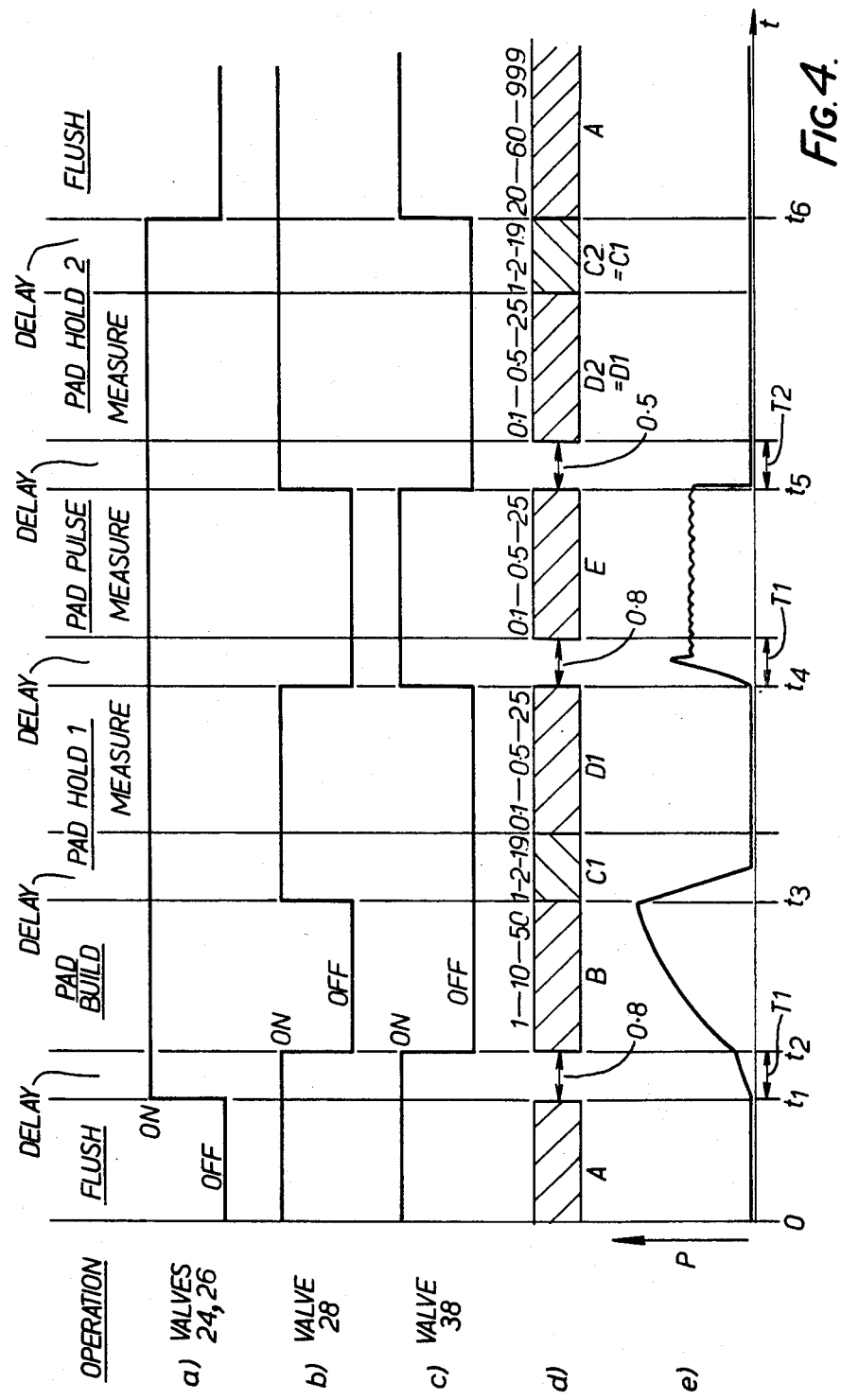
FIG. 4 shows a series of time diagrams illustrating the operation of the measuring cell.
Figure 5:
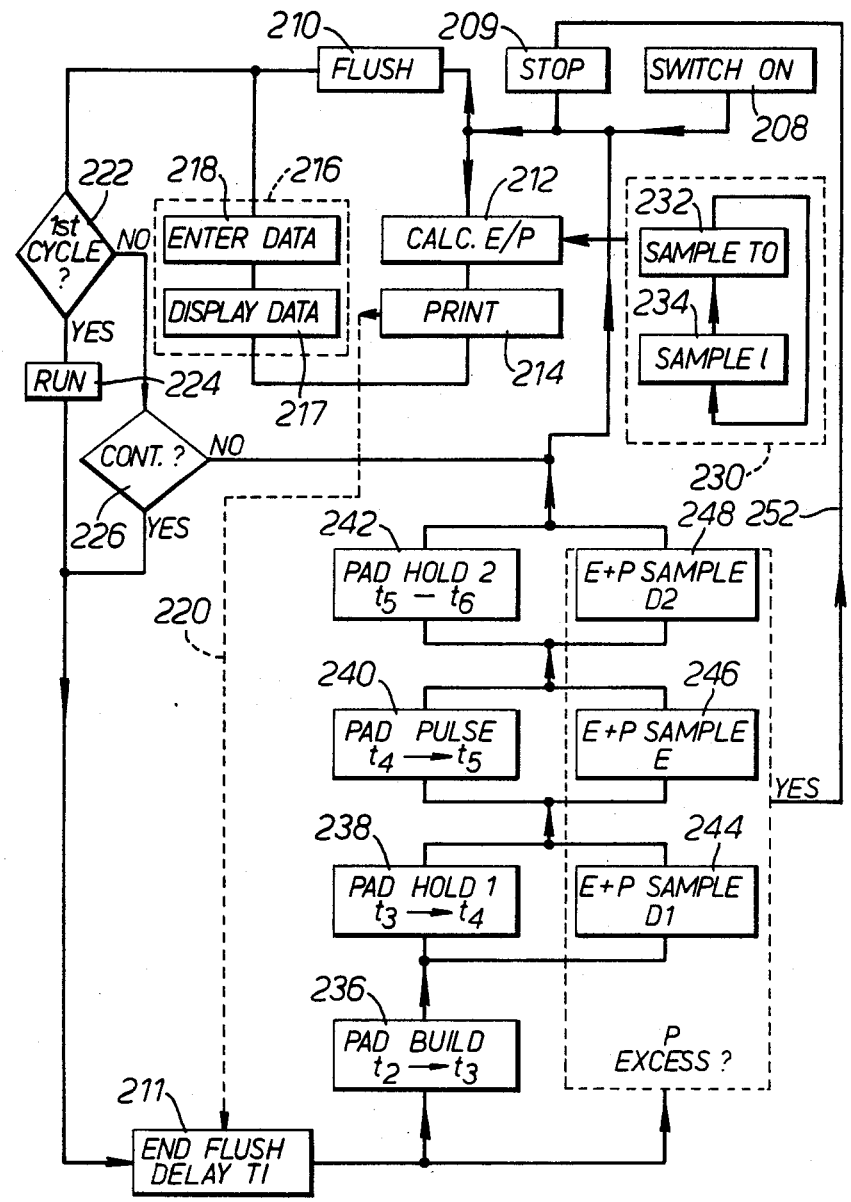
FIG. 5 is a simplified flow chart.

Having described the measuring cell 12 and its incorporation in the fluid circuit of FIG. 1, the actual measurement cycle will now be described with reference to FIGS. 3 to 5. FIG. 3 is a block electrical circuit diagram of the circuitry generally denoted as 140 in FIG. 1 which acts as both the control arrangement for the valves of FIG. 1 and the signal-processing arrangement for the various sensor signals. FIG. 4 shows timing diagrams for the sequences of operations carried in the measuring cycle and FIG. 5 is a related flow diagram for the major functions performed. The circuit 140 is based on a microprocessor which is programmed to perform both the control and measurement functions. Before describing the circuitry in greater detail, the functions to be performed will be set in context by a brief explanation of what is measured.

Streaming potential, E, across a fibrous plug or pad is given by the equation:

$$E = Z.P.e/4\pi.n.l. \tag{1}$$

where Z is the Zeta potential; P is the pressure across the pad, and e, l and n are respectively the dielectric contact, conductivity and viscosity of the feed stock. All quantities are in S.I. units.

Re-arranging this equation gives $$Z = (E/P) \cdot (4\pi . n . l / e).$$

The apparatus is operable to perform measuring cycles in which the ratio (E/P) is measured with the aid of the signals from the measuring cell 12. The other factors can be assumed to have set values or can themselves be measured and introduced into the calculation. In practice e (the dielectric constant of water), n and l can be separately measured or assumed constant. In practice, the re-arranged equation can be reduced to the form:

$$Z = K(T) . l . (E/P) \qquad (2)$$

where K(T) is a temperature-dependent constant that takes into account both e and n and their temperature dependence. The medium is, of course, assumed to be water.

What is measured therefore is the E/P ratio with temperature correction if desired to which a conductivity correction can also be added. In practical terms it is believed sufficient to obtain a consistent and reliable measure of the E/P or corrected E/P ratio without it being necessary to calculate the precise Zeta potential value.

Figure 3:
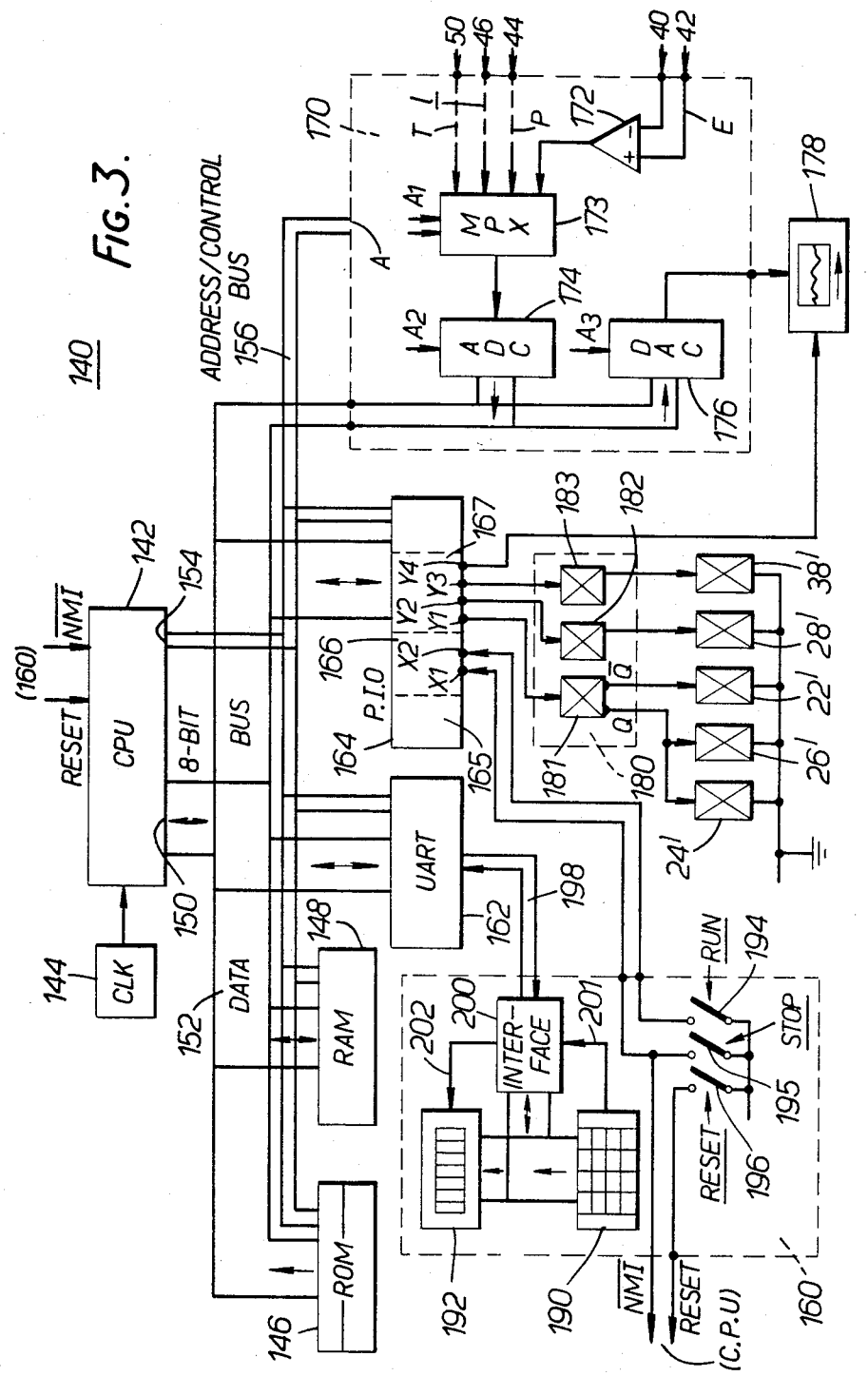
FIG. 3 is a block diagram of the electrical control and measuring circuit of the apparatus.

Referring now to FIG. 3, the circuit 140 is based on a microprocessor (e.g. a Zilog Z80) which controls the operating of the valves, the acquisition of data from the sensor elements of the measuring cell and the calculation of results based on the acquired data. The microprocessor is also responsive to input control signals to control the timing of stages of the measuring cycle.

Detail connections for the CPU and the associated circuitry are not shown. The purpose of FIG. 3 is to illustrate the organisation of the circuitry to bring out how the control and inputting of signal data is effected. Much of the circuitry can be realised with the aid of standard Z80 peripheral boards such as are available from Mostek along with appropriate data. There is of course much data published on the Z80 and its associated devices by Zilog, the manufacturers, and others.

Likewise it is not intended to give detailed programs. The description of operation given herein with the aid of FIGS. 4 and 5 will show the functional requirements and the realisation of the programs is well within the compass of those skilled in that art.

Referring to the circuit 140 of FIG. 3, the Z80 device provides the central processor unit (CPU) 142. Directly associated with the CPU is a clock 144, which not only drives the CPU but from which the timed sequence later described is derived, a Read Only Memory (ROM) 146 and Random Access Memory (RAM) 148. The CPU has an 8-bit data input/output port 150, which leads to a data bus 152. The CPU also has a 16-bit address port and various control terminals which are shown together as a single address/control port 154 which leads to an address/control bus 156. This bus also carries the clock signals from source 144 to the various peripherals. The ROM and RAM have their data ports connected to the data bus and are controlled by the CPU over the address/control bus.

Operator controls and displays are associated with a control panel 160 whose associated components are connected to the CPU via a UART (Universal Asynchronous Transmitter/Receiver) board arrangement 162 as far as data is concerned, the UART board being connected to the data and address/control busses 152 and 156. Also connected to these busses is a parallel input/output (PIO) board arrangement 164 which has three accessory ports 165, 166, 167 diagrammatically indicated as three sections of the arrangement 164. These ports provide access to the CPU for other peripheral devices and circuitry as will be set out hereinafter. Port selection in the PIO arrangement is managed over the address/control bus. Clearly only one port can be in data communication with the main data bus 156 at a time. One port 165 provides data and control access to a printer (not shown) that can be used to print data stored in RAM 148 and calculated results. In fact port 165 is a combination of two 8-bit ports providing data and control access respectively. This need not be discussed further. A second port 167 is used, inter alia, to control the valves 22, 24, 26, 28 and 38 of FIG. 1 whose solenoids-indicated by the use of a prime added to the reference number-are included in FIG. 3 for ease of understanding. As will be explained below, the five valves are controlled by three output terminals denoted Y1-Y3 in the figure by way of a relay arrangement 180. The third port 166 provides access to various push button switches on the control panel whose commands are input at terminals X1 and X2. In fact ports 166 and 167 can be realised by division of the eight terminals of a single port of the P.I.O. 164. The analogue board arrangement 170 receives the various analog signal inputs and provides an analog output of the calculated E/P ratio. Operation of the devices on the analog board is controlled by the CPU 142 via the address/control bus 156. As illustrated the board 170 has an address port A connected to bus 156 and to which address control inputs $A_1$, $A_2$ and $A_3$ of the devices to be described are connected (these connections are shown in a diagrammatic way). The board 170 has its own internal 8-bit data bus 171 connected directly to main data bus 152.

FIG. 3 as described thus far has been divided into four main areas: the CPU and its associated ROM and RAM connected to it by the data and address/control busses; what might be termed the operator related circuitry 160 connected primarily via UART interface 162; the valve control circuitry 180 connected via one port of PIO arrangement 164, and the analog circuitry 170 connected directly to the CPU. The circuitry and its operation will now be considered in more detail.

To control the apparatus of FIG. 1, the CPU controls the relay arrangement 180. This comprises three relays 181, 182 and 183 that control the valve solenoids. The relays may be of the conventional electro-mechanical type. The contacts are not shown as such. Valves 24 and 26 are always opened and closed together while valve 22 is always in the opposite state to these two valves. Thus the three valve solenoids 24', 26' and 22' can have their energisations controlled via one relay 181 whose opposed outputs are diagrammatically denoted Q and Q̄. The other two valve solenoids 28' and 38' are separately controlled by relays 182 and 183 respectively. The three relays 181, 182 and 183 are activated by CPU 142 through the three terminals Y1-Y3 of the port 167 of the PIO arrangement 164. The pump 32 runs continuously during the measuring cycle.

On the analog board, the streaming potential electrodes 40, 42 are connected to a differential buffer amplifier 172 typically having a gain of 100 and providing an output in the range ±5 V to the multiplexer, i.e. the streaming potential E can swing positive or negative. The buffer amplifier is designed to provide a high input resistance-not less than 10 Megohms. A typical resolution required for the potential E is 0.1 mV. The signals from the other sensors are adjusted by respective input circuitry (not shown) to lie in similar voltage ranges (±5 V for the board specified below) though they will all be of a single polarity. The pressure transducer 44 is operative over the range 0–5 bar with a resolution required of 0.01 bar. The temperature sensor 46 is operative over the range 0°–100° C. and the resolution required is 1° C. The conductivity sensor 48 is operative over the range 0–2000 micromhos and a resolution of 2 micromhos is required.

The sensor signals are applied to a multiplexer unit (MPX) 173 which is controlled by the CPU 142 to select any one signal input as required. The selected signal is then applied to an analog-to-digital converter (ADC) 174 also controlled by the CPU from which the digitised value of the selected analog signal and a polarity bit is sent to the CPU for storage in the RAM 148 for use in subsequent calculations of the E/P ratio. The board will include buffers (not shown) for transferring the ADC output in two bytes (high and low) onto the 8-bit bus for transfer into the RAM.

The circuit elements of the analog circuit 170 are all available on the Mostek board specified below, with the exception of the buffer amplifier 172. If any of the other input signals are to be buffered, separate buffers are needed. To minimise noise pick up the buffer amplifier 172 should be mounted as close to the cell as possible to keep leads short. The whole circuitry 140 of FIG. 3 may be located adjacent the cell. If the CPU is more remote, the analog board 170 and associated buffers can be mounted close to the cell so that only the digital signals have to be transmitted over a distance.

The CPU outputs the E/P ratio in digital form. This is converted into an analog signal by digital-to-analog converter (DAC) 176 for plotting on a chart recorder 178. The starting and stopping of chart movement is controlled by the CPU via terminal Y4 of the port 167.

Turning to the circuitry associated with the operator panel 160, it includes a hexadecimal keypad 190 and multi-digit display 192 of say seven digits of which the first, i.e. at the left, is used as a sign (polarity) indicator, the next is a hexadecimal display for codedly indicating the nature of what is being displayed, and the remaining five provide numerical data. The display assists the operator when entering data and the control program can be used to provide the operator with the current status of parameters stored in CPU registers. These will only be mentioned to the extent that they are relevant to an understanding of the sequence of operations of the apparatus.

The operator can establish certain parameters of the measuring cycle of the apparatus by use of the keypad 190. Such data entry is only recognised by the CPU during the flushing condition and is then used to control the timing of the sequence of operations to be described with reference to FIG. 4. The operator can also use the keypad to tell the CPU whether the measuring cycle is to be repeated continuously or whether a single sequence is to be run (single-shot operation).

In addition the control panel includes three push-button operated switches 194, 195, 196 associated with functions RUN, STOP, RESET respectively. The RUN button needs to be pressed to initiate a single-shot measurement or to initiate the first cycle of a continuous measurement. The switch 194 is connected to a terminal X2 of port 166 of PIO arrangement 164 so that its state can be polled by the CPU (a latching switch may be used). The STOP switch 195 enables the operator to interrupt a cycle and return the apparatus to the flushing condition. To this end the switch activates an interrupt input, designated $\overline{\text{NMI}}$ in the Z80, of the CPU 142. The switch is also connected to a terminal X1 of port 166 so that actuation of the switch is also signalled to the CPU to cause it to go to a sub-routine to put the apparatus into the flushing condition. The RESET switch is activated to signal the RESET input of the Z80 CPU. This input causes all program counters etc. to be set to zero, that is to put the whole program into an initial state. The CPU will go through an initialisation procedure to initialise all the peripherals and working memory. This includes entering the preset parameter values referred to below. It is to be understood that upon switch-on of the apparatus, the RESET of the CPU is activated. The initial state of the apparatus is in the flushing condition which may thus be regarded as the quiescent condition in the absence of instructions to proceed through the measuring cycle.

The data passing between the keypad 190 and display 192 and the CPU 142 is done by way of a serial transmission link requiring the conversion of parallel data to serial data for transmission and then back to parallel. Such conversion and the control of transmission and reception is done with the aid of a UART device. Such devices are readily available and need not be described in detail here.

The CPU data bus 152 is, therefore, connected to the UART interface arrangement 162 for the serial transmission and reception of data and control information, in for example RS232 format, over a link 198. To couple the link to the display and keypad, these have an internal serial input interface unit 200 associated with them which control, as indicated by connections 201 and 202, the reception of data from the keypad to transmit over link 198 and the transmission of parallel data to the display as received in serial form over the link. The keypad, display and associated serial interface unit are available as a single assembly from Burr Brown, Inc.—type No. TM 25 300 HT.

The sequence of operations carried out by the CPU under the program control to perform a measuring cyle will now be described with reference to FIG. 4 which is a set of time diagrams showing various of the operations and outputs as a function of time. FIGS. 4a–c show the states of the valves 24 and 26, 38 and 28 respectively during the measurement cycle. The operation of valve 22 is the inverse of FIG. 4a. FIG. 4d indicates at the shaded areas those phases within the cycle whose durations are operator selectable and the selectable duration phases are legended with the limits therefor (in seconds). FIG. 4e is a somewhat stylised representation of the pressure signal from the pressure transducer 44. The streaming potential E will follow a somewhat similar waveform.

As mentioned above the apparatus may be settable for "one shot" operation, that is, to be triggered to perform a single measurement cycle at the end of which the apparatus is left in the flushing condition, or to perform repeated cycles. Looking at the phases of the cycle illustrated in FIG. 4 in conjunction with FIG. 1, they are run automatically under the control program stored in ROM 146, the CPU calling up specific timing information as the program proceeds. This is timing information entered by the operator through keypad 190 or preset times in the absence of such data. With the cell 12 in the initial flushing condition, valves 22 and 28 are open and valves 24 and 26 closed so that clean water is flowing downwardly through the cell 12 to drain. Valve 38 is also open so that pump 32 merely pumps the small amount of stock bled from breastbox 30 through the loop 34. If the apparatus is in the second or later cycle of a continuous measurement selection, the time $t_1$ is the end of the selected flushing period. Otherwise, if this is the first cycle or the "single-shot" mode has been chosen, the RUN button switch 194 needs to be pressed to initiate further action. It should be noted at this point that if measurements of conductivity l and temperature T are wanted, they are made before the flushing condition is terminated and the results entered into RAM 148.

At time $t_1$ valve 22 is closed and simultaneously valves 24 and 26 opened. The pump 32 can now begin to pump a relatively small amount of feed stock upwardly into cell 12 though much will flow to drain through valve 28. The stock particles begin to deposit on filter mesh 14. After a delay of duration T1 the valves 28 and 38 are closed at $t_2$ so that pump 32 is pumping stock entirely to the cell 12 which exhausts to drain through valve 24. As the stock flows upwardly through cell 12 the pad or plug is built up by the fibres, fines etc. depositing on filter mesh 14 in what is called the pad-building phase. As the pad thickens, the pressure across it increases as is shown by the pressure waveform P.

The delay T1 is fixed at say 0.8 seconds. The period of pad-building indicated as B in diagram d is selectable between 1 and 50 seconds with a duration of 10 seconds in the absence of a specific selection by the operator.

Following the pad building phase, the valve 28 is opened at time $t_3$ so that the pressure in the lower portion of cell 12 falls rapidly (to a nominal zero) which condition is then held over a period called PAD HOLD 1. This period is divided into a first delay portion C1 which is followed by a measurement portion D1–diagram d–during which pressure P and streaming potential E measurements are made by sampling in the manner to be described. The delay C1 is to allow the cell 12 to stabilize in its low pressure condition before making measurements in the period D1. C1 is selectable between 1 and 19 seconds with a value of 2 seconds in the absence of a specific selection. D1 is settable between 0.1 and 25 seconds with a value of 0.5 seconds in the absence of a specific selection.

At time $t_4$, a pulse of constant pressure is applied to the cell 12 (the upper end of which is still connected to drain) by closing drain valve 28 and opening valve 38 to the restrictor. While the pressure pulses are each substantially constant within the pulse, there may be a pulse-to-pulse variation which is taken into account by the described measurement procedure. Another fixed delay of duration T1 is allowed for pressure transients to die down after valve switching so that during the following period E in diagram d a pressure pulse of a magnitude fixed by restrictor 36 is applied to the pad on filter mesh 14. The pulse measurement period E has its duration settable between 0.5 and 25 seconds with a value of 0.5 seconds in the absence of a specific selection. As will be seen from pressure waveform (e), the pressure pulse may have a ripple content which stems from the pumping action of pump 32. Should ripple be present, it does not significantly affect the calculated result using the sampling measurement technique to be described.

It will be noted that the duration E may extend to 25 seconds. Although during this period negligible further accumulation of material to the pad will occur—that is there is substantially no flow through the cell—the duration E should normally be chosen small relative to the pad building period B. The pre-selected values will be noted to be in the ratio of 0.5 to 10 seconds respectively.

Following measurements on the pad at fixed pressure, at time $t_5$ the restrictor valve 38 is closed and the lower drain valve 28 opened to return the lower portion of cell 12 to nominal zero pressure. After a fixed delay T2—say 0.5 seconds—to allow the cell pressure to stabilize, a second pad hold period PAD HOLD 2 is entered. Further measurements are made at the nominal zero pressure over the first portion D2 of this period. D2 is made equal (in the program) to that of the first zero pressure measurement period D1. Following this measurement period there is another delay C2 whose duration equals that of period C1. Thus C2 and D2 mirror C1 and D1 and simplify the number of entries to be made in the program timing. Thereafter at time $t_6$ valves 24 and 26 are closed, and the clean water inlet valve 22 and the valve 38 opened. Drain valve 28 is already open to allow the pad to be released from the mesh 14 pressure of the water above it and to be removed from the cell by the water flowing into the top of cell 12. As previously discussed the internal structure including cone 122 is designed to ensure as far as possible that the pad and any residual particles are washed from the mesh and all the material completely flushed to drain. The flushing phase has a duration A—diagram d—settable between 20 and 999 seconds (999 seconds is about 16½ minutes) with a value of 60 seconds in the absence of a specific selection. This only applies if the apparatus is set for repetitive cycling. If operating in the "one-shot" mode then the apparatus remains in the flushing mode until next triggered to begin a new measurement cycle.

The measurement cycle described involves a sequence control which could, for example, be done with cam operated switches of the multiple rotary cam-operated type. The realisation of the sequence under microprocessor control will be readily understood by those skilled in programming. The adoption of microprocessor control has the advantage of making the periods A to E in diagram d readily adjustable, the program calling up the period selected as the cycle is run or otherwise acting on the pre-set figure if no specific data has been entered.

The adoption of microprocessor control also has advantage in the making of measurements because it allows storage of substantial numbers of measurements and calculations therefrom.

It will be recalled that what is being determined is the E/P ratio and that this ratio may be corrected in accord with equation 2) for the temperature dependance of the viscosity and dielectric constant of the water. Correction may also be made for conductivity. Ignoring the conductivity and temperature corrections for the moment, consideration will first be given to the measurement of streaming potential E and pressure P via the electrodes 40, 42 and pressure sensor 44 in cell 12 for derivation of the basic E/P ratio.

In the measuring cycle illustrated in FIG. 4 there are three measurement periods D1, E and D2, two of which D1 and D2 are of equal duration at the nominal zero pressure level and lie either side of the third E at the pressure pulse level. During these measurement periods the CPU (FIG. 3) controls the multiplexer switch to take a series of alternating readings of potential E and pressure P which are digitised by ADC 174 and the digital values stored at known locations in the RAM. The measurements are timed from the microprocessor clock 144 and during each measuring period, each of the parameters E and P is sampled at 0.01 second intervals. As the maximum length of a period is 25 seconds up to 2500 samples of each of E and P may be taken. To avoid the need for substantial amounts of RAM storage, the program may be arranged to store only up to the first 2 seconds of measurement samples in one period, i.e. 200 samples. These may be then printed out during the flushing period. The RAM storage is limited so that the E and P values are accumulated (summed) from the start of each measurement period in the working memory of the CPU. This operation will also involve counting of the number of items summed so that average values may be readily calculated.

After the three measuring periods of a cycle have ceased the CPU calculates the E/P ratio during the next flushing period.

To this end the average E and P values for the pressure pulse period E are calculated with reference to their values during the nominal pressure zero periods D1 and D2, i.e. the mean pulse height of the P and E signals. If we call these values $P_m$ and $E_m$, the average of the P and E measurements in period D1, $P_1$ and $E_1$ respectively, the average P and E in period D2, $P_2$ and $E_2$ respectively, the average P and E in pulse period E, $P_y$ and $E_y$ respectively, then $$\left. \begin{array}{l} P_m = 2P_y - P_1 - P_2 \\ E_m = 2E_y - E_1 - E_2 \end{array} \right\} \quad (3)$$

Thus the average P and E values on the right of the equation are readily calculated from the summed P and E values accumulated for each period and dividing by the number of values as would be established in the relevant counters in the working memory. Consequently the E/P ratio calculated is $E_m/P_m$. By using this sampling and averaging technique, pressure pulsations in the pulse period E or of other small disturbances, do not significantly affect the result.

If conductivity and/or temperature are to be corrected for, then the correction is applied to the basic $E_m/P_m$ ratio.

Temperature correction is applied by means of a look-up table which can be stored in ROM 146 (FIG. 3). Referring to equation 2, the factor K(T) is stored for 5° steps. If temperature correction is applied the temperature in cell 12 is measured with the aid of temperature sensor 46 after the CPU initiates the FLUSH operation at $t_6$ (FIG. 4). The temperature is taken to the nearest 5° point. The table is set out below.

| T | K | T | K | T | K | T | K |
|---|---|---|---|---|---|---|---|
| 0 | 1.626 | 5 | 1.414 | 10 | 1.245 | 15 | 1.111 |
| 20 | 1.000 | 25 | 0.909 | 30 | 0.833 | 35 | 0.768 |
| 40 | 0.714 | 45 | 0.666 | 50 | 0.626 | 55 | 0.590 |
| 60 | 0.559 | 65 | 0.531 | 70 | 0.506 | 75 | 0.484 |
| 80 | 0.466 | 85 | 0.449 | 90 | 0.434 | 95 | 0.421 |

-continued

| T | K | T | K | T | K | T | K |
|---|---|---|---|---|---|---|---|
| 100 | | | | | | | |

Thus to obtain a temperature-corrected reading the calculation $K(T) \cdot E_m/P_m$ is made. If the operator has instructed that no temperature correction is to be made the uncorrected ratio $E_m/E_p$ will be for an assumed temperature of 20° C. for which K(T)=1.

Finally if conductivity compensation is required, a conductivity measurement is made with the aid of sensor 48, also after the time $t_6$. The value obtained is divided by 500 and the result used as a further correction factor L(=1/500) by which the basic, or already temperature-corrected, $E_m/P_m$ ratio is multiplied. L is a number which represents a normalisation of the measured conductivity value to 500 micromhos. If the CPU is instructed by the operator not to correct for conductivity, a value of L=1 is assumed, i.e. an assumed conductivity of 500 micromhos. In this case K(T) could be adjusted to include an allowance for the temperature dependence of the conductivity.

The taking of averages over the measurement periods smooths out short term fluctuations so that the result is not unduly influenced by them. Pressure is also monitored outside the actual measurement periods in order to detect any excess pressure potentially damaging to the cell. Pressure is measured during the pad build up period and the three measuring periods. To this end the pressure sensor is continually sampled from the time $t_2$ (FIG. 4) at 0.01 second intervals (including the measurement samples) until the end of measurement period D2 and each digital value obtained checked to ascertain if it exceeds a value corresponding to a predetermined maximum pressure. With the cell 12 described the maximum pressure limit is set at 4 bars. If the limit is exceeded the CPU stops the measurement cycle (equivalent to pressing the STOP button), the apparatus then going into the flushing phase and an error indication provided on the display 192. Any results obtained in that cycle up to the moment it is stopped are discarded.

In order to summarize the main elements of the control and measurement programs executed by the CPU 142, reference may be made to the flow chart of FIG. 5 in which the main elements are set out. FIG. 5 should be taken in conjunction with FIG. 4.

The quiescent (flushing) phase 210 is entered upon switch on—step 208—, pressing the STOP button (or equivalent operation)—step 209 or at the end of a measurement cycle. In the latter case, in parallel with the CPU establishing the flushing condition, it calculates at step 212 the E/P ratio, with correction if previously so instructed, and then prints out results including information stored in the RAM 148 (FIG. 3) at step 214. The E/P ratio can also be plotted on chart recorder 178 at this time. Although the RAM storage of sample values is limited, normally each sample of values for a measurement period will be representative of the whole period. The RAM storage is conveniently arranged so that the corresponding E and P values are stored in pairs and can be extracted and printed out in pairs. These may be used for example for subsequent statistical analyses.

Following these operations the keyboard 190 is made available to the operator as indicated by step 216 to call up data stored in the memory or to enter in parameter data. These steps are shown as 217 and 218 respectively but may be taken in any order. For example, in calling up data all current mean values of streaming potential and pressure may be requested or the current values of temperature and conductivity (further mentioned below). This may be done by pressing selected ones of the numerical keys of the hexadecimal keypad set in accordance with a prescribed code. The values are then displayed on display 192.

For data entry the following may be entered:

durations of periods A, B, C (i.e. C1=C2), D (i.e. D1=D2) and E of FIG. 4d:

selection of continuous or "single-shot" operation:

selection of temperature correction:

selection of conductivity correction. The period durations can be selected by, for example, pressing that hexadecimal key that bears the legend corresponding to the above notation of the period and entering the numerical value required to 0.1 second.

The other selections which each involve two choices are entered by pressing appropriate keys in accord with a prescribed code and then entering a "0" or "1" dependent on the choice selected.

This data entry is displayed as entered and the data stored in the memory associated with the CPU for use in performing the program. Out of range selections of periods A to E cause an error display.

If the flushing period is between cycles of continuous mode operation, then the period will have a selected value and if it ends before the operator has entered all the data he wants, the next cycle resumes with the data entered up to the end of the flushing period. However, the pressing of a key following the end of the flushing phase is noted by the CPU and causes an error display at the end of the measuring cycle. However, the flushing phase will not be terminated if it is sufficiently short to not allow time for print out step 214. In this case flushing is held until the end of print out is signalled. The action to end flushing is shown as a separate step 211 and its dependence upon the termination of printing indicated by dash line 220. A consequence of the mode of establishing operating parameters described is that existing parameters are retained until fresh ones are properly entered.

To proceed with the program the CPU checks at step 222 whether the flushing phase 210 is preceding the first cycle of a measurement. This check is initiated while the flushing phase is in progress. If this is the first cycle of a continuous mode operation or if it is to be the first and only cycle of a single-shot operation, i.e. the answer to the check is YES, then no further action is taken until the RUN button switch 194 is activated—step 224. Otherwise the flushing phase continues. Should check 22 reveal this is not the first cycle, a decision is then made as indicated by step 226 on the basis of whether the continuous or single-shot mode has been selected. If in continuous mode (YES) the program continues with the next measurement cycle. If in the single-shot mode (NO) the apparatus is returned to the quiescent flushing condition.

When the cycle continues or the RUN button is pressed, the flushing phase can then be terminated which is indicated as the specific step 211 occurring at time $t_1$ in FIG. 4. This action which is followed by the fixed delay T1, is then followed by the main phase of pad building at $t_2$ in FIG. 4.

The successive steps in FIG. 4 of PAD BUILD, PAD HOLD 1, PAD PULSE and PAD HOLD 2, including their relevant delays, are shown as the sequence of steps 236, 238, 240 and 242 in FIG. 5. In parallel with steps 238, 240 and 242 the sample values of streaming potential E and pressure P are taken for calculation purposes as steps 244, 246 and 248 respectively corresponding to measuring intervals D1, E and D2 of FIG. 4. The timing of these steps will proceed on the basis of any specific selection data entered via the keypad at step 218. Otherwise the internally stored preset values will be used.

As PAD BUILD step 236 commences, the pressure monitoring step 250 also commences and continues until the end of the PAD HOLD 2 phase. The step is shown to embrace sampling measurement steps 244, 246 and 248 since in regard to pressure, the pressure samples taken for these steps will be used both for calculation and for monitoring. If an excess pressure is detected, then as shown by line 252, the equivalent of a STOP signal 209 is generated to interrupt the program and cause the CPU to execute a routine returning the apparatus to the flushing condition. An indication of this is generated on display 192.

Assuming no excess pressure problems arise, after the PAD HOLD 2 stage, the program returns the apparatus to the flushing condition and in parallel therewith, the CPU calculates the E/P ratio in accord with the data accumulated in the preceding cycle and the instructions previously fed in. In order to act on instructions to include temperature and/or conductivity in achieving an E/P ratio, values of these two parameters have to be taken. This may be done in various ways, for example by including measurement steps in the main operating cycle. It is presently preferred however to perform these measurements as a separate continuous routine 230 which includes continual sample measurements of temperature T in step 232 and conductivity l in step 234. When instructed to act on one of these parameters the CPU enters the last sample value into the calculation of the corrected E/P ratio, this value being taken prior to flushing commencing.

The calculated E/P ratio is conveniently displayed on display 192 while being made available for print out, if required, at which time the DAC 176 (FIG. 3) is activated to provide the corresponding signal to chart recorder 178. The chart paper movement may be controlled by the CPU, for example, by advancing it only during the period $t_2$ to $t_6$, so that if the cycle is stopped for any reason, the paper advance also ceases.

Figure 6:
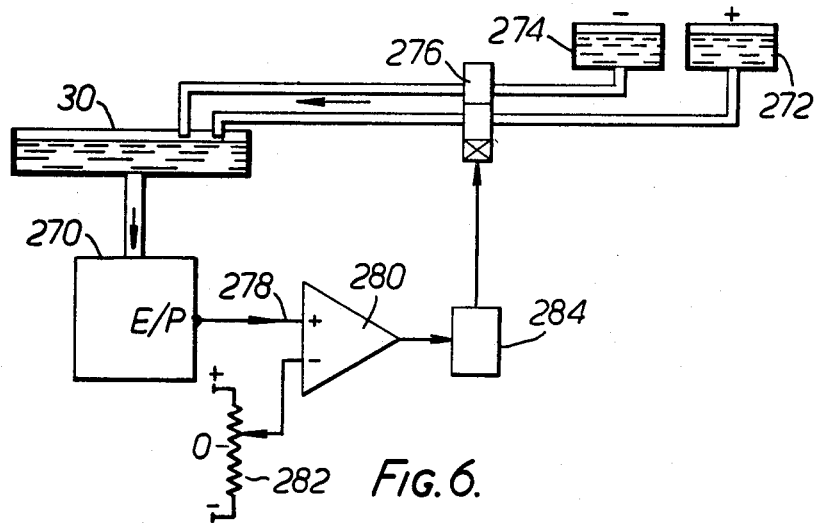
FIG. 6 shows in diagrammatic form a control system for a paper-making machine incorporating the measuring apparatus to regulate Zeta potential in the feed stock.

FIG. 6 shows how the E/P ratios may be applied in a paper-making machine so as to control the value to zero or other set value.

The apparatus described is shown as block 270 operating in continuous mode and making measurements on the stock tapped from breastbox 30. The stock may be supplemented with cationic and anionic additives from sources 272 and 274 respectively under the control of valve assembly 276. The E/P ratio, e.g. the analog value supplied by DAC176 (FIG. 3) is fed on line 278 to a comparator 280 where it is compared with a preset value derived from a potential divider 282 that may be set to zero or to a positive or negative value as considered appropriate to the paper being formed. The comparator produces an error output which is used to control the valve assembly 276 via appropriate drive circuitry 284. The assembly is designed to block both additive sources for zero or low error and to progressively open one source or the other dependent on the polarity and magnitude of the error to supply a corrective additive to the feed stock. Because the E/P measurement is intermittent, the control system will in fact cause the instantaneous ratio to fluctuate about the desired value. The E/P signal used could, of course, be the digital version with the use of a digital comparator.

Reverting to the apparatus of FIG. 3 a substantial part of the circuitry can be realised with standard Z80 boards available from Mostek Inc. and data on the boards is likewise available from that company. For example, a CPU board (MDXCPU) with facilities for plug-in ROM and RAM is available under the type No. MK77853. The UART arrangement 162 is available on a board (MDX EPROM/UART) type No. MK77753-4 to which a debug facility can be added. The PIO arrangement 164 is realisable with a four port board (MDX PIO) type MK77654. As already mentioned the keypad/display is available as a unit type No. TM25 300HT from Burr-Brown, Inc.

The general organisation and operation of the apparatus described with reference to FIGS. 3 to 5 can be adapted to other CPU devices currently available.

The microprocessor and its associated peripheral chips, RAM and ROM could all be realised using single chip microcomputer with inbuilt ADC and DAC. Such devices are available from various manufacturers, e.g. Intel.

The display and keyboard could also be under direct control of the CPU instead of communicating over a serial link.

There will now be described some modifications of the cell 12 of FIG. 2 which enable the cell structure and assembly to be simplified and filter changing made easier.

Figure 7:
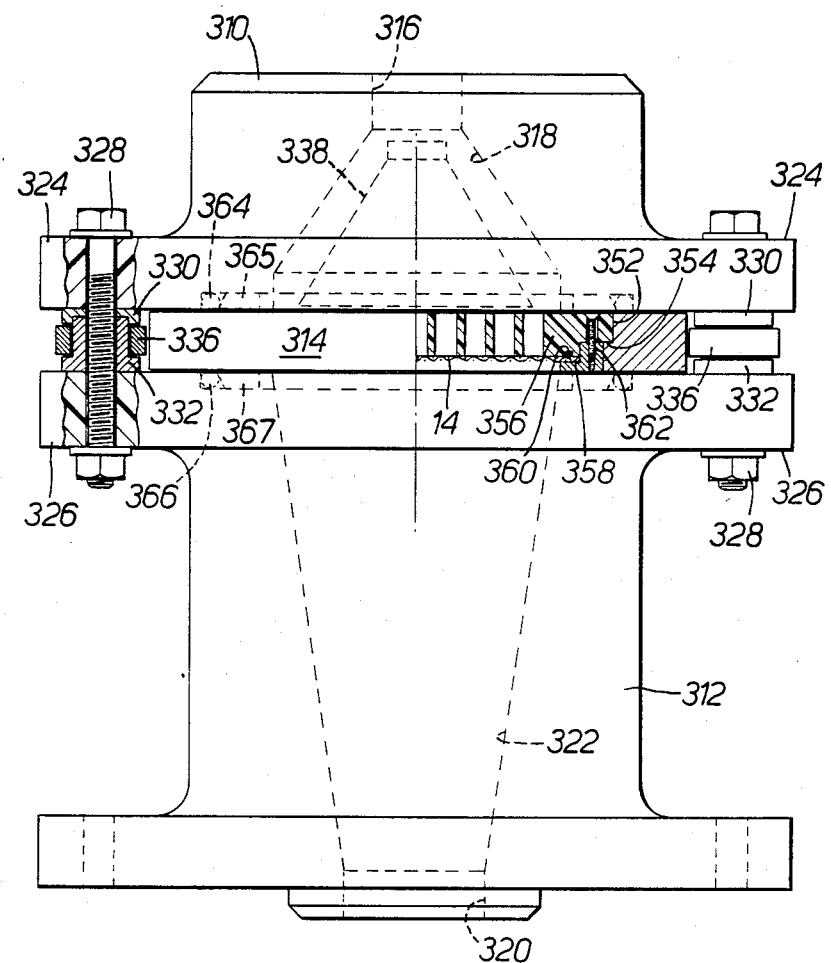
FIGS. 7 and 8 show electrical views, part-sectioned, of a modified cell providing a slidable filter carrier assembly for greater ease of filter changing, FIGS. 7 and 8 being taken normal to and in the direction of sliding movement respectively.
Figure 8:
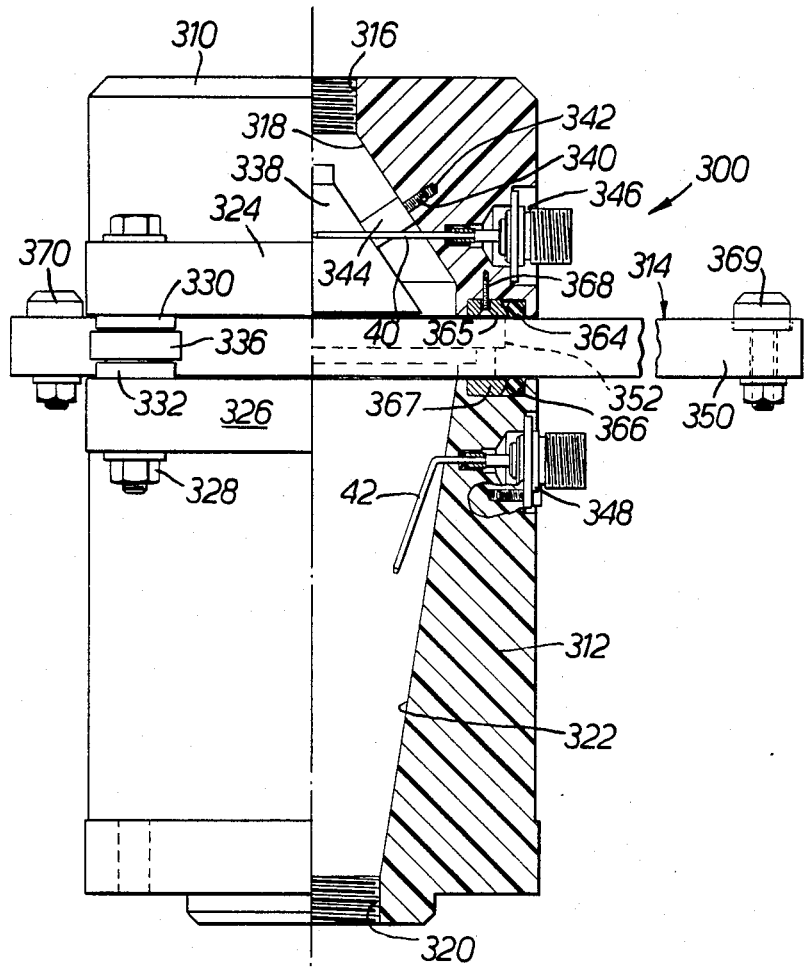
Figure 9:
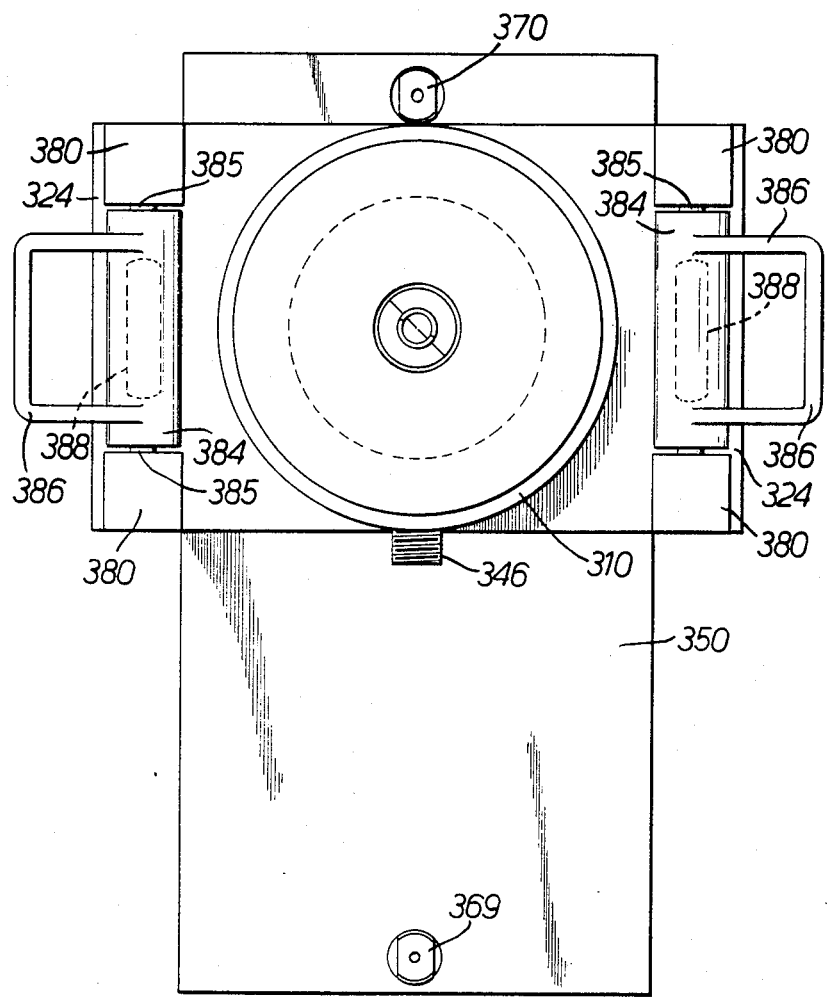
FIG. 9 is a top plan view of a cell similar to that of FIGS. 7 and 8 but having a modified release mechanism for the filter carrier assembly shown in the release position.

FIGS. 7 and 8 show part-sectioned elevations looking respectively in and normal to the direction of movement of a filter carrier assembly. The cell 300 comprises upper and lower housing members 310 and 312 between which the filter carrier assembly 314 is located. Reference may be made to FIG. 9 for a plan view of the upper member 310 and the assembly 314, although FIG. 9 itself shows a further modification to be described below. The upper housing member 310 is machined from a block of perspex which has an axial port 316 (conduit fittings are not shown) leading to a shallow, inverted, frusto-conical surface 318. The lower housing member 312 is likewise machined from a block of perspex and has an axial port 320 leading to a more acute frusto-conical surface 322 coaxial with surface 318 and having an apex angle of about 9°. This general interior configuration follows that of FIG. 2 defining upper and lower compartments.

Each of the housing members 310 and 312 has a pair of integral flanges, 324 and 326 respectively, located on opposite sides of the member extending normal to the plane of FIG. 7 and in opposed relationship to the flanges of the other member. The pairs of opposed flanges lie to one side and the other of the filter carrier assembly in its direction of movement. The flanges are secured by four nut and bolt combinations 328 one at each flange corner and are spaced apart by a pair of interfitting, hollow pillar members 330, 332 located on each bolt and defining a recess 334 on which a roller 336 is rotatable to guide the filter carrier assembly described below.

Similarly to the structure of FIG. 2 the upper housing member 310 has a conical deflector or flow distributor 338 in the upper compartment. The distributor is apertured and spaced inwardly from the periphery of the filter to establish the flow of flushing fluid as previously described. In this embodiment the distributor 338 is secured by six equi-angular disposed studs one of which is shown in FIG. 8. The stud 340 engages a threaded bore 342 in the conical surface of the housing member 310 and carries a spacer 344 to hold the distributor 338 in correct position.

Each of the upper and lower housing members 310 and 312 is formed to receive a respective bushing 346 and 348 from which a stainless electrode 40 and 42 projects into the respective interior compartment for sensing streaming potential.

It will be seen that by virtue of the pillars 330, 332 the upper and lower housing members are spaced apart. In this space the slidable, filter carrier assembly 314 is received. The assembly comprises an elongate planar carrier 350 best seen in FIGS. 8 and 9. The figures show the assembly in the operative position. The left-hand end portion of the carrier 350, as seen in FIG. 8, contains a circular aperture 352 the periphery of which is stepped at 354 to receive and locate the complementarily stepped periphery of a circular filter support disc 356 which is perforated to allow free flow therethrough as described for corresponding disc 70 in FIG. 2. The disc 356 carries the wire mesh 14 on its under surface. The peripheral margin of the mesh 14 is trapped between a lower step 358 of the carrier 350 and the margin of disc 356 with the aid of an annular O-ring seal 360 to prevent leakage past the periphery. The thickness dimension of the disc 356 is such that it seats in aperture 352 to provide a flush upper surface with carrier 350 and the disc 356 is secured in the carrier at its periphery by a number of countersunk screws 362 one of which is shown.

The facing surfaces of upper and lower housing member 310 and 312 have opposed rebates of greater diameter than the interior chamber and which locate respective O-ring seals 364 and 366 that engage the upper and lower surfaces of the carrier to encircle the aperture 352 and close the interior chamber. Distortion and possible displacement of the seals 364 and 366 is prevented by annular inserts 365 and 367 respectively that are secured by screws 368 one of which is seen in FIG. 8. Sealing engagement between the seal rings and the carrier surfaces surrounding the aperture 352 is obtained when the nut and bolt combinations 328 are tightened, the spacer pillars preventing undue compression. This is the condition illustrated in FIGS. 7 and 8. The cell is ready for use in the manner already described.

To change a filter, the housing does not need to be dis-assembled. The nuts and bolts are slackened sufficiently to allow the carrier 350 to be moved to the left as seen in FIG. 8, the carrier being guided by the rollers 336 engaging its long sides. The carrier is made long enough to move the disc 356 out of the housing whereby the screws 362 may be released to allow the disc 356 and mesh 14 to be lifted out of aperture 352. The procedure is reversed with a new wire mesh 14 fitted. Each end of the carrier 350 is provided with a respective stop 369 and 370. Stop 369 prevents the carrier from being slid right out of the hosing on changing a filter. Stop 370 abuts the housing in the operative condition and thus serves to ensure correct location of the filter in the interior chamber.

Figure 10:
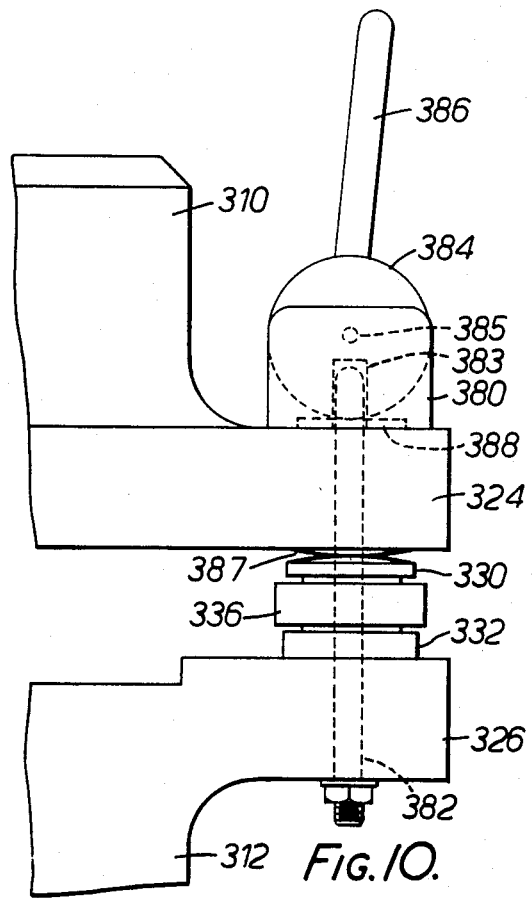
FIG. 10 shows a detail of the release mechanism of FIG. 9 shown in the locked position.

A further modification of the release mechanism for enabling sliding movement of the filter assembly is shown in FIGS. 9 and 10. FIG. 9 is a plan view showing the outline of the upper housing member 310 and the carrier assembly 314 with its elongate carrier plate 350. Instead of a simple nut and bolt fastening at each flange corner, the upper housing flanges 324 carry a boss 380 at each corner. As better seen in the detail of one corner of FIG. 10, a threaded stud 382 extends through aligned apertures in the lower and upper flanges and is engaged in a threaded bore 383 at the base of the boss. Each stud carries the spacing pillar members 330, 332 supporting the roller 336 and in this modification further carries a pair of bowed spring washers 387. Referring again to FIG. 9 also, between the pair of bosses 380 on each flange 324 is mounted a circular cylinder 384 that is journalled to each boss as shown at 385, the journal being off-centre of the cylinder axis so that the cylinder rotates eccentrically. The cylinder carries an actuating handle 386 for rotating the cylinder. Between the bosses 380 on each flange a respective thrust plate 388 is mounted to be acted upon by the cylinder.

The cylinders 384 act as eccentric cams. As the handles are moved from a near horizontal position shown in FIG. 9 to an upright position of FIG. 10 the eccentricity causes the cylinders to increasingly bear on the thrust plates 388 squeezing the facing pairs of flanges 324, 326 together against the action of the spring washers 387 to lock the carrier plate 350 in a sealed operative condition such as shown in FIGS. 7 and 8. Release of the carrier plate to slide it to the filter changing position simply requires that the handles 386 be moved to the horizontal position.

What is claimed is:

1. A measuring apparatus for use in the measurement of an electrical characteristic of a fibrous dispersion comprising:

a measuring cell having a housing defining a hollow interior, upper and lower ports in said housing to allow fluid to be passed therethrough in a generally vertical direction, and an essentially horizontally disposed filter mesh in said housing dividing said interior hollow into upper and lower compartments, and a respective electrode in each of said compartments for measuring the streaming potential generated in the cell; and respective first and second fluid conduit arrangements connected to said upper and lower ports respectively, the first conduit arrangement including respective connections for a source of flushing fluid and drain and valve means for controlling the flow of fluid through said connections, and the second conduit arrangement including respective connections for a source of particle-bearing stock and drain, and valve means for controlling the flow of fluid through these last mentioned connections, whereby stock enters the cell to build a pad of particles on the underside of the filter mesh and the pad is subsequently flushed from the filter mesh to drain through said lower port.

2. A measuring apparatus as claimed in claim 1 in which said measuring cell further comprises a hollow inverted frusto-conical member in said upper compartment, said member having apertures in the conical wall thereof to distribute flushing fluid entering said upper port axially to the central part of the filter mesh and to outer portions of the filter mesh through said apertures in order to remove a pad formed on the filter mesh.

3. A measuring apparatus as claimed in claim 1 in which the housing of said measuring cell defines the interior hollow to have an intermediate section in which said filter mesh is supported, an upper end section of frusto-conical form narrowing upwardly to said upper port and a lower end section of frusto-conical form narrowing downwardly to said lower port.

4. A measuring apparatus as claimed in claim 1 in which said measuring cell comprises an upper housing section defining an interior frusto-conical surface narrowing upwardly to said upper port, a lower housing section defining an interior frusto-conical surface narrowing downwardly to said lower port, an intermediate section located between said lower and upper sections and comprising a carrier member having an aperture at which said filter mesh is receivable, means at said aperture for locating said filter mesh to cover said apeture, and said locating means providing for dismounting of said filter mesh therefrom, the carrier member being mounted for reciprocal sliding movement between a first position in which the filter mesh is disposed between said upper and lower housing sections and a second position at which the filter mesh is located to one side of said upper and lower housing sections, and said carrier means including stop means defining the limits of said reciprocal movement, one limit being said first position, and respective sealing means acting between said carrier member and said upper and lower housing sections to provide a sealed enclosure for the filter mesh in said first position.

5. A measuring apparatus as claimed in claim 4 in which said carrier member is of planar elongate form and slidable between facing surfaces of said upper and lower housing sections, said aperture is located at one end portion of said carrier member and said sealing means are respective annular seals carried in recesses in said facing housing surfaces to encircle said aperture and engage the surrounding carrier member surfaces in said first position.

6. A measuring apparatus as claimed in claim 5 further comprising releasable means acting between the upper and lower housing sections and movable between a stable activated position to engage said carrier member firmly with said seals to ensure the sealing action of said sealing means in said first position of said carrier member, and a stable released position facilitating sliding movement of said carrier member to its second position.

7. Apparatus as claimed in claim 6 in which said upper and lower housing sections have flanges extending on and to one side of said carrier member with respect to its direction of movement, said releasable means acting between the flanges.

8. Apparatus as claimed in claim 4 in which said measuring cell further comprises a hollow inverted frusto-conical member in said upper compartment, said frusto-conical member having apertures in the conical wall thereof, and means supporting said frusto-conical member in spaced relation with the interior frusto-conical surface of said upper housing section, whereby said frusto-conical member promotes the distribution of flushing fluid entering said upper port over said filter mesh from the center to the periphery thereof to remove a pad formed thereon.

9. A measuring apparatus as claimed in claim 1 in which said measuring cell further comprises a pressure transducer responsive to the pressure in said lower compartment.

10. A measuring apparatus as claimed in claim 1 in which said valve means of the first conduit arrangement comprises first and second valves connected between said upper port and respectively said flushing fluid connection and drain connection, and the valve means of said second conduit arrangement comprises third and fourth valves connected between said lower port and respectively said feed stock connection and drain connection, and wherein said second conduit arrangement comprises a pump connected between said feed stock connection and said third valve for pumping feed stock to said lower port, and a flow diversion path comprising restrictor means and a fifth valve connected between said pump and third valve for establishing a predetermined pressure determined by said restrictor means.

11. A measuring apparatus as claimed in claim 10 further comprising control means coupled to said first to fifth valves to control the actuation thereof in a predetermined sequence including the steps in which (a) said second and third valves are open and said first, fourth and fifth valves are closed to allow feed stock to be pumped upwardly through said measuring cell to drain to thereby form a pad on said filter mesh;

(b) said second, third and fifth valves are open and said first and fourth valves are closed to establish a pressure determined by said restrictor means in said lower cell compartment to act upon the pad on the filter mesh;

(c) said first and fourth valves are open and said second and third valves are closed to cause flushing fluid to flow downwardly to drain thereby removing the pad and flushing the material thereof to drain; and (d) said second, third and fourth valves are open and said first valve is closed at least once prior to the flushing to establish a low pressure reference condition in said lower cell compartment.

12. A measuring apparatus as claimed in claim 11 for the measurement of streaming potential as said electrical characteristic, in which said measuring cell further comprises a pressure transducer responsive to the pressure in said lower compartment, and the apparatus further comprising signal processing means connected to said electrodes and said pressure transducer, said signal processing means being operable to take measurements of streaming potential and pressure during step (b) and during step (d) and to calculate a measure of the ratio of streaming potential to pressure during step (b) referred to the values obtained in step (d).

13. A measuring apparatus as claimed in claim 12 in which said signal processing means is operable to respectively sample the streaming potential and pressure values during each step and to perform the calculation using averages obtained from the repetitive sampling in each step.

14. A method of obtaining a measure of streaming potential using a measuring cell having a housing defining a hollow interior, upper and lower ports in said housing to allow fluid to be passed therethrough in a generally vertical direction, and an essentially horizontally disposed filter mesh in said housing dividing said hollow interior into upper and lower compartments, a respective electrode in each compartment for measuring streaming potential generated in the cell, and a pressure transducer responsive to pressure in said lower compartment, the method comprising the steps of:

(a) introducing feed stock containing particulate material to said lower port to flow upwardly through the cell and develop a pad of such material on said filter mesh;

(b) applying a pressure pulse to said pad and measuring the streaming potential across said electrodes and the pressure in said lower compartment;

(c) reducing the pressure across the pad to substantially zero at least once, and measuring the streaming potential and pressure in the lower compartment at each occurrence of the substantially zero pressure; and determining the ratio of streaming potential to pressure in step (b) where the values in step (b) are taken relative to the values obtained in step (c).

15. A method as claimed in claim 14 in which said measurements of streaming potential and pressure in the respective steps are performed by taking a series of measurements and averaging the measurements taken in each series.

16. A method as claimed in claim 14 in which a temperature measurement is taken and the ratio of streaming potential to pressure is corrected by multiplying same by a temperature-dependent factor.

17. A method as claimed in claim 14 in which a measurement of fluid conductivity is taken and the ratio of streaming potential to pressure is multiplied by a conductivity-dependent factor normalized to a predetermined conductivity value.

18. A method as claimed in claim 16 in which a measurement of fluid conductivity is taken and the ratio of temperature corrected streaming potential to pressure is multiplied by a conductivity factor normalized to a predetermined conductivity value.

19. A measuring cell comprising, in an upright position, an upper housing section defining an interior frusto-conical surface narrowing upwardly to an upper port, a lower housing section defining an interior frusto-conical surface narrowing downwardly to a lower port, an intermediate section located between said lower and upper sections and comprising a carrier member having an aperture at which a filter mesh is receivable, means at said aperture for locating said filter mesh to cover said aperture, and said locating means providing for dismounting of said filter mesh therefrom, the carrier member mounted for sliding movement between a first position in which the filter mesh is disposed between said upper and lower housing sections and a second position at which the filter mesh is located to one side of said upper and lower housing sections, and said carrier means including stop means defining the limits of said reciprocal movement, one limit being said first position, and respective sealing means acting between said carrier member, and said upper and lower housing sections to provide a sealed enclosure for the filter mesh in said first position.

20. A measuring cell as claimed in claim 19 in which said carrier member is of planar elongate form and slidable between facing surfaces of said upper and lower housing sections, said aperture is located at one end portion of said carrier member and said sealing means are respective annular seals carried in recesses in said facing housing surfaces to encircle said aperture and engage the surrounding carrier member surfaces in said first position.

21. A measuring cell as claimed in claim 20 further comprising releasable means acting between the upper and lower housing sections and movable between a stable activated position to engage said carrier member firmly with said seals to ensure the sealing action of said sealing means in said first position of said carrier member, and a stable released position facilitating movement of said carrier member to its second position.

22. A measuring cell as claimed in claim 21 in which said upper and lower housing sections have flanges extending on and to one side of said carrier member with respect to its direction of movement, said releasable means acting between the flanges.

23. A measuring cell as claimed in claim 19 in which said measuring cell further comprises a hollow inverted frusto-conical member in said upper housing section, said frusto-conical member having apertures in the conical wall thereof, and means supporting said frusto-conical member in spaced relation with the interior frusto-conical surface of said upper housing section, whereby said frustoconical member promotes the distribution of flushing fluid entering said upper port over said filter mesh from the center to the periphery thereof to remove a pad formed thereon.

* * * * *